United States Patent [19]

Berndt et al.

[11] Patent Number: 5,281,825
[45] Date of Patent: Jan. 25, 1994

[54] PHASE FLUOROMETRY USING A MODULATED ELECTROLUMINESCENT LAMP AS A LIGHT SOURCE

[75] Inventors: Klaus W. Berndt, Baltimore; Joseph R. Lakowicz, Columbia, both of Md.

[73] Assignee: The University of Maryland School of Medicine

[21] Appl. No.: 755,232

[22] Filed: Sep. 5, 1991

[51] Int. Cl.⁵ .............................................. G01J 1/58
[52] U.S. Cl. .............................. 250/458.1; 250/459.1
[58] Field of Search .................... 250/458.1, 459.1; 356/318, 417; 315/169.3

[56] References Cited

U.S. PATENT DOCUMENTS

| | | | |
|---|---|---|---|
| 4,633,141 | 12/1986 | Weber | 315/169.3 |
| 4,705,952 | 11/1987 | Lindmayer | 250/483.1 |
| 4,778,593 | 10/1988 | Yamashita et al. | 209/3.1 |
| 4,877,965 | 10/1989 | Dandliker et al. | 250/458.1 |
| 4,889,690 | 12/1989 | Oritz et al. | 250/458.1 |
| 4,895,156 | 1/1990 | Schulze | 128/634 |
| 5,030,420 | 7/1991 | Bacon et al. | 422/82.07 |

OTHER PUBLICATIONS

Wolfbeis et al "A new group of Fluorescent pH-Indicators for an extended pH -range", Fresenius Z. Anal Chem (1987), V. 327 pp. 347-350.
Moreno et al., ". . . pH Sensitive Optical Fiber Sensor . . . "; J. Mole Struc. 143 (1986) p. 553.
Guthrie et al. "Solid-State . . . Optical Fiber Chem Sensor"; Talanta, 35, 2 (1988) p. 157.
Ohkuma et al., "Luminescence Probe . . . of Intralysosomal ph . . . " Proc. Natl. Acad. Sci (75) 1978, p. 3327.
Lippitsh et al., ". . . Oxygen Sensor with the Fluorescence Decay Time as the Inform. Carriers", Anal. Chim Acta, 205 (1988) 1-6.
Berndt et al "Phase-modulation Fluorometry using a . . . laser diode light source" Rev. Sci. Instrum. 61(7) p. 1816 (1990).

Primary Examiner—Paul M. Dzierzynski
Assistant Examiner—Richard Hanig
Attorney, Agent, or Firm—Sughrue, Mion, Zinn, Macpeak & Seas

[57] ABSTRACT

A method and apparatus for using a square wave- or sinewave-driven electroluminescent lamp (ELL) as a source of periodically pulsed excitation light for a luminescent molecule, wherein changes in decay time, phase angle and/or modulation of the emitted luminescence are detected as parameters that correspond to changes in luminescence lifetimes.

55 Claims, 4 Drawing Sheets

PHASE FLUOROMETRY USING A MODULATED ELECTROLUMINESCENT LAMP AS A LIGHT SOURCE

FIELD OF THE INVENTION

The invention relates generally to the field of spectoscopy and, more particularly, to a method and apparatus for using an electroluminescent lamp (ELL) as a source of excitation light for a luminescent molecule, wherein changes in decay time, phase angle and/or modulation of the emitted luminescence are detected as parameters that correspond to changes in luminescence lifetimes.

BACKGROUND OF THE INVENTION

Luminescence is the emission Of photons from electronically excited states. Luminescence can include fluorescence and phosphorescence. In phosphorescence, e.g., from phosphorescent molecule, the photon emission is produced when the excited electrons go from an excited triplet state to an excited singlet state, with the time of return to the ground state from the excited singlet state being relatively long ($\mu$sec to sec). In fluorescence, e.g., from a fluorophore, the photon emission is from the excited singlet state to the ground state, and the time required for the return from the excited state to the ground state, is relatively short, with times as short as several nanoseconds and as long as many microseconds. The time required for luminescence photon emission in conjunction with the excited electron's return to the ground state is called the lifetime or decay time.

As used herein, Iuminescencell (or "photoluminescence") refers to one or more of fluorescence, phosphorescence and other photon emissions that are the result of excited elections returning towards the ground state, and "luminescent molecule" refers to a fluorophore, a phosphorescent molecule or a molecule that emits photons when the molecules excited electrons return towards a ground state when excitation is caused by a light source.

In solutions that are at or near room temperature, a variety of molecular events can occur within the nanosecond to microsecond time scale of luminescence which can alter the emission from a luminescent Molecule. Such events can be detected for sensing of analytes by analysis of changes in emission intensity or wavelength, and, in certain cases, by measuring the lifetime of the fluorophore as it changes due to quenching or enhancing effects of an analyte or acceptor molecule that binds an analyte.

In general, sensing of analytes has been conducted using intensity and wavelength shift fluorometry using laser light sources by well-known methods, such as sensing pH using intensity and wavelength shift absorption methods. For example, Moreno et al *J. Molec. Struct.* 143:553 (1986) describes the fluorescence absorption of cresol red to measure pH; Guthrie et al *Talanta* 35:157 (1988) uses absorption at two wavelengths via an LED optical pH sensor; Ohkuma et al *Proc. Nat'l Acad. Sci. USA* 75:3323 (1978) uses fluorescence for pH based on the ratio of intensities at different excitation wavelengths.

Additionally, ph-sensitive fluorophores for intensity or wavelength shift measurements have been described by Saari et al *Anal. Chem.* 54:823 (1982), which discloses ph-dependent intensity measurements of fluorescein; Wolfbe-Ls et al *Fresenius Z. Anal. Chem.* 327:347 (1987), which describes pH sensitive probes with varying pH ranges for intensity of: wavelength shift measurements; Offenbacher et al *Sensors and Actuators* 9:73 (1986), which discloses sensors requiring short wavelength excitation; Wolfbeis et al *J. Heterocyclic Chein.* 22:1215 (1985), which discloses a variety of pH sensors fol: intensity based measurements; and Wolfbeis et al *Fresenius; Z. Anal. Chem.* 314:119 (1983), which summarizes fluorescence pH sensors for intensity measurements.

Electroluminescent lamps are potential alternatives to laser light sources, due to the high cost, large size and difficulty in calibration and maintenance of laser light sources. Such alternatives offer the potential for more practical commercial applications in clinical and diagnostic medicine, as well as basic research, due to decreased size, cost, calibration and maintenance.

However, such alternative light sources, when used for intensity- or wavelength shift-based fluorometry, still suffer from the same problems when using intensity- or wavelength shift-based fluorometry with laser light sources, as described herein.

For example, an intensity-based, quenching detecting apparatus is described by Opitz e al. in U.S. Pat. No. 4,889,690. According to this patent, the concentration of oxygen in a sample of water was determined by effectively measuring the oxygen's quenching effect on the intensity of fluorescent radiation emitted by the fluorophores. The fluorescent indicators were excited by continuous light from a luminescent light source, such as a chemoluminescent or an electroluminescent light source, and the intensity of the resulting emitted light radiation (fluorescence) was measured by a photoelectric receiver.

However, the precise and accurate measurement of known intensity- or wavelength shift-based, sensing has suffered from problems such as delayed results, the need for expensive, sophisticated and time consuming procedures that are limited, e.g., by high background noise, low signal-to-noise ratios, turbidity, losses, high light absorbance, photobleaching and fluorophore washout.

Additionally, Lippitsch et al (*Anal. Chim. Acta* 205:1-6 (1988)) describe the use of the ruthenium complex tris (2,21'-dipyridyl) ruthenium (II) dichloride hydrate, embedded in silicone, as the active sensing membrane for determination of oxygen quenching of fluorescence lifetimes. The long unquenched sensor fluorescence lifetime of 205 ns in the absence of oxygen allowed the authors to use a relatively inexpensive blue-emitting LED as the excitation light source. However, since the optical output power of the commercially available blue-emitting silicon carbide LEDs is rather low, extremely sensitive (and expensive) light detectors, such as photomultipliers, are required to measure the emitted fluorescence radiation.

All of the above problems have the potential to be eliminated by the use of apparatus and methods wherein changes in decay time, phase angle and/or modulation of emitted luminescence are detected as parameters that correspond to changes in luminescence lifetimes, rather than to changes in luminescence intensity.

SUMMARY OF THE INVENTION

It is therefore an object of the present invention to overcome the above problems relating to luminescence detection by providing apparatus and methods in which an electroluminescent lamp (ELL) is used as a source of pulsed or high frequency modulated excitation light for a luminescent molecule wherein changes in decay time, phase angle and/or modulation of the emitted fluorescence are detected as parameters that correspond to changes in fluorescence lifetimes.

It is another object of the present invention to provide apparatus and methods using an excitation light source, such as an electroluminescent lamp driven by a sine-wave or square-wave driving signal, which can be modulated over a wide range of frequencies, or used as a pulsed light source, for detecting changes in decay time, phase angle or Modulation of an emission of an excited luminescent molecule corresponding to a change in lifetime, as a determination of a condition, wherein the change is caused by the presence or concentration of an analyte, or other environmental change of the luminescent molecule.

It is another object of the present invention to provide apparatus and methods that utilize an ELL for time-domain, frequency-domain or phase/modulation measurements of luminescence.

Another object of the present invention is to provide methods and apparatus using an ELL as a light source for measuring the presence or concentration of an analyte by utilizing luminescence lifetimes, such as analyte concentrations in cell and/or fermentation cultures.

Another object of the present invention is to provide methods of using an ELL for sensing analytes, using changes in luminescence lifetimes that are directly responsive to an analyte.

According to one aspect of the present invention, an apparatus is provided for detecting a change in decay time, phase angle and/or modulation, corresponding to a change in a lifetime, of a luminescent emission of at least one luminescent molecule comprising:

an electroluminescent lamp which outputs modulated light when driven by a first electrical signal;

a first electrical signal generator, coupled to the electroluminescent lamp, for generating the first electrical signal to cause the electroluminescent lamp to output the modulated light having a wavelength which excites the at least one luminescent molecule in a sample to produce the luminescence emission;

a photosensor for detecting the luminescence emission to generate a second electrical signal corresponding to the luminescence emission;

a meter coupled to said photosensor for comparing the first electrical signal and the second electrical signal to provide the change in decay time, phase angle and/or modulation of the luminescence emission of at least one luminescent molecule, wherein the change in decay time, phase angle or modulation corresponds to the change in at least one luminescence lifetime of the luminescent molecule.

In one embodiment, the electroluminescent lamp outputs the modulated light with a plurality of frequency components that are harmonics of the first electrical signal. In another embodiment, the wavelength of the modulated light is in the range of 250–1000 nm.

In still another embodiment, the output modulated light is intrinsically or extrinsically modulated, e.g., by square wave or sinusoidally modulated, at a frequency range of about 1 kHz to 10 MHz and the driving signal frequency is at least about 500 Hz.

In another embodiment, the photosensor is optically coupled to the luminescence emission via a lens system or proximity focused geometry, and the luminescent molecule has a lifetime of at least 25 nanoseconds.

In still another embodiment, the first electrical signal is a square wave signal, the first electrical signal is modulated at a fundamental frequency of at least 500 Hz, a third electrical signal is generated by a second electrical signal generator synchronized to the first electrical signal, and the second electrical signal generator is a frequency multiplier or frequency generator.

In another embodiment, the first electrical signal is a sine wave signal, the first electrical signal is modulated at a fundamental frequency of at least 10 kHz, and the third electrical signal is synchronized with the first electrical signal.

In another embodiment, the photosensor is preferably a positive insulating negative (IIPINII) photodiode. The photosensor may also be a photomultiplier tube, a photodiode, a large-area photodiode, an avalanche photo diode or a charge coupled device.

In another aspect of the present invention, a spectroscopy method is provided that uses an electroluminescent lamp as a high-frequency modulated light source, the method comprising detecting a change in decay time, phase angle and/or modulation, corresponding to a change in a lifetime, of a luminescence emission of at least one luminescent molecule.

In one embodiment, the change in decay time, phase angle and/or modulation corresponds to the presence of an analyte, such that the method provides for sensing the analyte.

According to another aspect of the present invention, a method is provided for detecting a change in decay time, phase angle and/or modulation, corresponding to a change in a lifetime, of a luminescence emission of at least one luminescent molecule comprising:

driving an electroluminescent lamp with a first electrical signal to cause the electroluminescent lamp to output modulated light having a wavelength which excites the at least one luminescent molecule in a sample to produce the luminescence emission;

exciting at least one luminescent molecule with the modulated light to produce a luminescence emission;

detecting the luminescence emission with a photosensor to produce a second electrical signal corresponding to the luminescence emission;

comparing the first electrical signal to the second electrical signal to provide the change in decay time, phase angle and/or modulation of the luminescence emission of at least one luminescent molecule, wherein the change corresponds to the change in a luninesence lifetime of the luminescent molecule.

In one embodiment, the electroluminescent lamp outputs the modulated light with a plurality of frequency components that are harmonics of twice the fundamental frequency of the first electrical signal and the wavelength of the modulated light is in the range of 250–1000 nm.

In still another embodiment, the output of the modulated light is intrinsically or extrinsically modulated at a frequency range of 200 Hz to 10 MHz, or preferably 1 kHz to 10 MHz.

In another embodiment, the photosensor is optically coupled to the fluorescence emission via a lens system or proximity focused geometry, and the fluorophore has a lifetime of at least about 25 nanoseconds.

In still another embodiment, the first electrical signal is a square wave signal, the first electrical signal is modulated at a fundamental frequency of at least 500 Hz, and the output of the modulated light is intrinsically or extrinsically modulated at a frequency range of 1 kHz to 10 MHz.

In another preferred embodiment, the third electrical signal is generated by a second electrical signal generator synchronized to the first electrical signal, the second electrical signal generator is a frequency multiplier or frequency generator.

In another embodiment, the first electrical signal is a sine wave signal, the first electrical signal is modulated at a fundamental frequency of at least 10 kHz, and the third electrical signal is synchronized with the first electrical signal.

In another embodiment, the photosensor comprises a first photodiode, and the first photodiode comprises a PIN photodiode. In another embodiment, the photosensor comprises at least one selected from a photomultiplier tube, a photodiode, a large area photodiode, an avalanche photodiode, and a charged coupled device.

In another embodiment, the change in decay time, phase and/or modulation corresponds to the presence or concentration an analyte in a sample, wherein the sample is a compound, a mixture, a surface, a solution, an emulsion, a suspension, a mixture, a cell culture, a fermentation culture, a cell, a tissue, a secretion or a derivative or extract thereof.

In another embodiment, the analyte comprises a salt, a derivative, a polymer, a dissociation product, or aggregate of the analyte, and the analyte is selected from $H^+$, $OH^-$, $CO_2$, $Na^+$, $Mg^{++}$, $H_2CO_3$, $HCO_3^-$, $Ca^{++}$ or $K^+$.

In another embodiment, the method comprises a frequency-domain luminescence lifetime measurement, a time-domain luminescence lifetime measurement, a phase angle lifetime measurement, a phase-sensitive luminescence lifetime measurement, or a modulation luminescence lifetime measurement.

Further advantages and features of the invention will become apparent from the following description, claims, and drawings, which are directed to preferred embodiments of the invention.

DESCRIPTION OF PREFERRED
EMBODIMENTS OF THE INVENTION

In recent years, the preferred light source for intensity- and lifetime-based fluorometry has become a laser light source. Owing to their high peak power, these lasers allow efficient frequency doubling over extended wavelength ranges, yielding tunable short-wavelength excitation radiation. Additionally, as described above, LED's and luminescent lamps have been used in limited methods to measure changes in intensity or quenching due to the presence of oxygen.

As noted above, however, intensity-based fluorometry methods suffer from problems such as delayed results, the need for expensive, sophisticated and time consuming procedures that are limited, e.g., by high background noise, low signal-to-noise ratios, turbidity, losses, high optical density, photobleaching and fluorophore washout. These problems can be minimized or eliminated by the use of a measuring system based on luminescence lifetime (or decay) measurements which are insensitive to changing instrument conditions and which are independent of the intensity fluctuations of luminescence radiation.

In the context of the present invention "luminescence" refers to one or more of fluorescence, phosphorescence and other photon emission caused by the return of excited electrons towards the ground state. Additionally, the term "luminescent molecule", as used in the context of the present invention, refers to a fluorophore, a phosphorescent molecule or a molecule that emits photons when the molecules excited electrons return towards a ground state when excitation is caused by an ELL light source according to the present invention.

According to the present invention, a modulated semiconductor ELL is provided which is a superior alternative to excitation-light sources such as LED'S, coherent wave lasers and dye lasers. Additionally, an ELL according to the present invention can be operated in a pulsed mode, producing harmonics of the pulse repetitive rate.

Apparatus and methods according to the present invention provide an ELL as an inexpensive excitation light source for spectroscopy. A modulated electrical input to the ELL causes a very large number of photons to be emitted so that inexpensive light detectors may be used to measure emitted luminescence. A square-wave or sine-wave (sinusoidal) driving input to the ELL can be used according to the present invention to produce light pulses having a repetition rate equal to twice the driving frequency and other harmonics thereof.

Accordingly, the overall optical output power produced by the ELL is much higher than the output of known LED'S, such as blue-emitting LEDS.

Additionally, as an ELL can be manufactured with a large light-producing area, less sensitive (and less expensive) light detectors (such as photodiodes) can be used to detect luminescence emissions over a relatively large area, e.g., up to 100cm² or higher. Similarly, ELL's can be used to illuminate multiple or extended samples simulataneously or sequentially, such as samples contained in a 96-well assay or culture dish. Therefore, extremely sensitive and expensive luminescence detectors, such as photomultipliers, are not required, but can also be used in spectroscopy apparatus and methods according to the present invention.

Accordingly, the present invention provides apparatus and methods for a luminescence lifetime-based measuring system which has improved accuracy and sensitivity, but without the high cost of expensive known light sources and light detectors, and which provides increased total light intensity with substantial modulation at twice the driving frequency and other harmonics thereof.

Additionally, the present invention provides apparatus and methods for a measuring system which is based on luminescence lifetimes, which is insensitive to changing instrument conditions and which is independent of the intensity fluctuations of fluorescence radiation.

Furthermore, in contrast to laser diodes and other laser sources, the light from an ELL can be distributed over a relatively large area, resulting in less intense local light intensity and fewer problems associated with local sample homogeneity.

Also, methods and apparatus according to the present invention solve some of the same problems associated with the use of a semiconductor laser diode as a light source, e.g, as described in U.S. patent application No. 07/695,074 (the entire contents of which are incorporated herein by reference), which problems include relatively low intensity light output at excitation wavelengths, due to the need for frequency doubling in order to provide excitation light at frequencies corresponding to the excitation wavelengths of the fluorophores used.

In the context of the present invention, the term "sample" refers to opaque, clear or turbid compounds, mixtures, surfaces, solutions, emulsions, suspensions, mixtures, cell cultures, fermentation cultures, cells, tissues, secretions and/or derivatives or extracts thereof.

Such samples to be measured according to the present invention require only that the luminescent molecule used be contacted with the sample such that the analyte to be sensed influences the lifetime of the luminescent molecule such that a decay time, phase angle and/or modulation, corresponding to the lifetime, of the emitted luminescence of the excited luminescent molecule reproducibly varies with the presence or amount of the analyte.

Accordingly, luminescent molecules used in a sample containing an analyte to be detected or measured according the present invention include free, bound, imbedded or fixed luminescent molecules, such as solutions, emulsions, suspensions, luminescent molecules ionicly or covalently bound to other compounds or materials, enclosed in permeable or nonpermeable membranes, embedded in polymers or other suitable materials, and the like, so long as the luminescent molecule is in sufficient proximity to the analyte so that the lifetime of the luminescent molecule is reproducibly altered by the presence of the analyte.

Such samples containing analytes to be detected according to the present invention can also include, e.g., animal tissues, such as blood, lymph, cerebrospinal fluid (CNS), bone marrow, gastrointestinal contents, and portions, cells or internal and external secretions of skin, heart, lung and respiratory system, liver, spleen, kidney, pancreas, gall bladder, gastrointestinal tract, smooth, skeletal or cardiac muscle, circulatory system, reproductive organs, auditory system, the autonomic and central nervous system, and extracts or cell cultures thereof. Such samples can be measured using methods of the present invention in vitro, in vivo and in situ.

These samples can also include environmental samples such as earth, air or water samples, as well as industrial or commercial samples such as compounds, mixtures, surfaces, aqueous chemical solutions, emulsions, suspensions or mixtures.

Additionally, samples that can be used in methods of the present invention include cell culture and fermentation media used for growth of prokaryotic or eukaryotic cells and/or tissues, such as one or more of bacteria, yeast, mammalian cells, plant cells and insect cells.

The term "analytell in the context of the present invention refers to elements, ions, compounds, or salts, dissociation products, polymers, aggregates or derivatives thereof. Examples of analytes that can be used in methods of the present invention include, $H^+$, $OH^-$, $CO_2$, $H_2CO_3$, $HCO_3^-$, $K^+$, $Ca^{++}$, $Na^+$, $Mg^{++}$ ions or other compounds containing these ions or compounds, including salts, derivatives, polymers, dissociation products, or aggregates thereof.

Luminescent molecules suitable for use in methods according to methods of the present invention include luminescent molecules whose lifetimes vary reproducibly with a condition of the microenvironment, such as the concentration or amount of a particular analyte, as described herein, and which lifetimes are detectable by known spectroscopy methods. It has been discovered that luminescent molecules, previously known to vary by intensity or wavelength shifts in response to the presence or concentration of an analyte, also vary in lifetime in response to the presence of the same analyte. Preferably, luminescent molecules to be used according to the present invention have lifetimes of at least about 25 ns. Fluorophores suitable for use in the present invention can also have much longer lifetimes, e.g., up to milliseconds.

Accordingly, luminescent molecules suitable for use in methods and apparatus of the present invention include luminescent molecules that have luminescence lifetimes which vary continuously over a suitable range of analyte concentrations or amounts, and that are excitable with a suitable light source, such as an ELL light source at a corresponding excitation wavelength. In one preferred embodiment, such lumninescent molecules have excitation wavelengths in the ultraviolet, near infrared (NIR) or visible light range. In another preferred embodiment, such luminescent molecules have excitation wavelengths in the ranges of about 250 to 1000 nm.

Examples of suitable luminescent molecules for use in the present invention include ruthenium and lanthanide containing molecules.

Thus, the present invention provides for apparatus and methods for condition sensing or detecting of a sample, such as analyte sensing, using detection of a change in decay time, phase angle and/or modulation (relative to the lack of presence of the analyte), corresponding to a change in lifetime, of luminescence emission of a luminescent molecule, and includes all luminescent molecules meeting the above criteria.

Therefore, luminescent molecules suitable for use in methods and apparatus of the present invention are not limited to the types and examples described herein.

The entire contents of copending applications by Joseph R. Lakowicz and Henry Szmacinski entitled METHOD FOR OPTICALLY MEASURING CHEMICAL ANALYTES, and U.S. patent application No. 7/695,074, entitled FLUOROMETRY METHOD AND APPARATUS USING A SEMICONDUCTOR LASER DIODE AS A LIGHT SOURCE, both filed May 3, 1991, are herein incorporated by reference, as well as are copending U.S. applications, Ser. Nos. 07/595,343, entitled METHOD AND APPARATUS FOR PERFORMING PHASE FLUORESCENCE LIFETIME MEASUREMENTS IN FLOW CYTOMETRY, filed Oct. 10, 1990; and 07/645,525, entitled METHOD AND APPARATUS FOR MULTI-DIMENSIONAL PHASE FLUORESCENCE LIFETIME IMAGING, filed Jan. 24, 1991.

For a luminescent molecule with a single-exponential luminscence decay, the measured phase shift angle, $\theta$, depends on the luminescence lifetime, Y, and on the modulation frequency, f, according to the following expression:

$$\tan\theta = 2\pi f y \quad (1)$$

For a given error in measuring $\theta$, maximum lifetime measurement accuracy can be established by optimizing the modulation frequency of the light source. From equation (1), it follows that the optimum modulation frequency, $f_{opt}$, is given by the following expression:

$$2\pi f_{opt} Y = 1 \quad (2)$$

For example, in the case of the above ruthenium complex with an unquenched luminescence lifetime of 205 ns, equation (2) yields an optimum modulation frequency of 777 kHz. For shorter lifetimes caused by oxygen quenching of the luminescence, even higher frequencies would be required.

Lifetimes can also be measured from the modulation of the emission relative to the modulation of the excitation. The modulation, m, is related to the lifetime, Y, by $$m = (1 + (2\pi f Y)^2)^{\frac{1}{2}} \quad (3)$$

In general, luminescence lifetime measurement accuracy is increased by optimizing the modulation frequency of the ELL light source by choosing the appropriate harmonic of the ELL pulse frequency. As shown in the equations (1)–(3) above, the luminescence lifetime is monitored by measuring the phase shift and/or modulation of the luminescence emission relative to the phase and/or modulation of the modulated exciting light. Thus, even luminescence chemical sensors with decay times as short as 25 ns can utilize an inexpensive ELL as a excitation light source according to the present invention. Additionally, higher harmonics of the pulse repetition frequency can also be preferably generated to conduct a phase shift and/or modulation measurement.

The application of a square-wave signal to an ELL produces output light pulses having a repetition rate equal to twice the input frequency. The shortest pulses obtained have a rise time range of about 250 ns, a decay time of 1.5 $\mu$s, and a full width at half maximum (FWHM) of 1 $\mu$s.

Thus, the high rate of change from positive to negative voltage of the square-wave input signal causes the ELL to emit a pulsed light output at a high repetition frequency. As a result, a very large number of photons is emitted by the ELL, thereby providing a relatively high optical output power. Thus, less sensitive (and less expensive) luminescence detectors, such as photodiodes, can be used as detectors for measuring a change in decay time, phase angle and/or modulation of emitted fluorescence of at least one fluorophore, wherein the change corresponds to a change in luminescence of the luminescent molecule, due the presence of an analyte, to be detected.

In accordance with the present invention, an ELL device can serve as a modulated exciting light source for phase-modulation when used in the sinusoidally-modulated mode, or when pulses are generated by a square-wave input, so that the fluorescence decay times (lifetimes) can be measured by the above phase-angle method.

Alternatively, time-domain methods can be used, e.g., as disclosed in U.S. Pat. Nos. 4,877,965 (Dandliker et al) and 4,895,156 (Schulze), the entire contents of which are incorporated by reference. However, the above phase and/or modulation methods are preferred, as further described below.

If the driving signal is a sine-wave voltage, the driving signal frequency should be such that short ELL light pulses are obtained, preferably at a frequency of at least about 10 kHz. If the driving signal is a square-wave signal, the transition time between a positive voltage and a negative voltage can be preferably less than or equal to about 1 ms, preferably about 1 $\mu$s.

Figure 1:
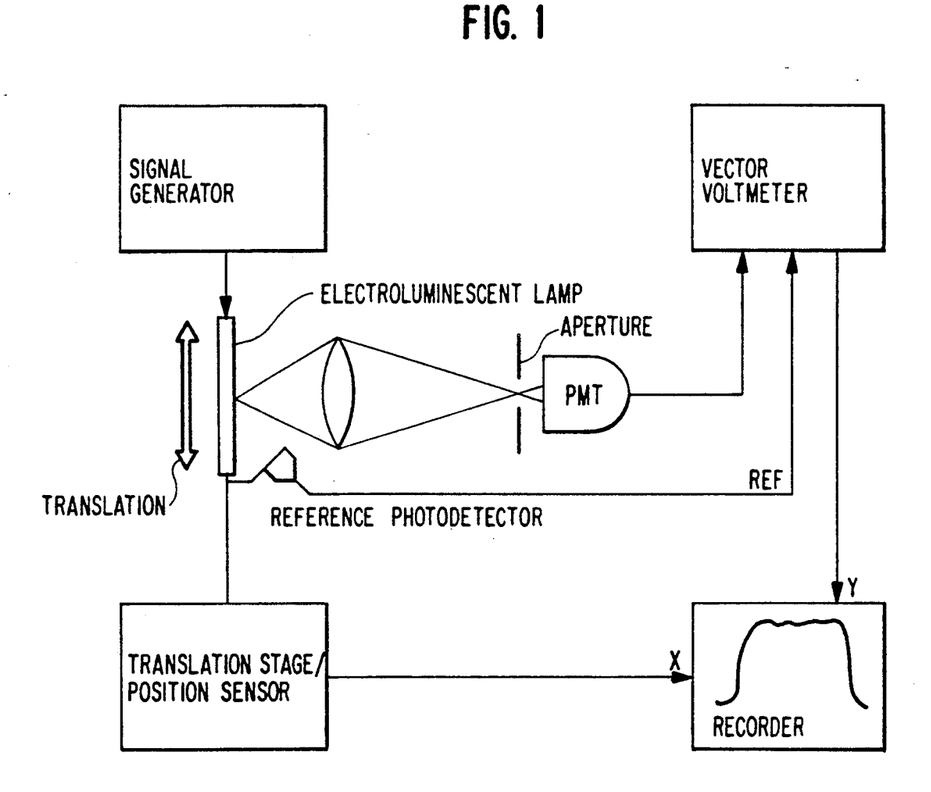
FIG. 1 is a semi-schematic diagram of a testing system for measuring the spatial phase and modulation behavior of intensity-modulated large-size ELLS.
Figure 2:
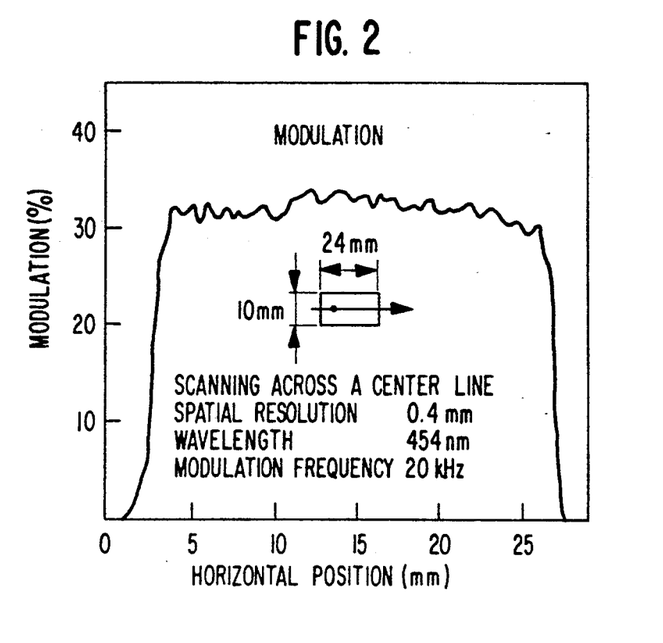
FIG. 2 is a graph of light-modulation versus horizontal position across a light-emitting area for a 454 nm violet-emitting Perma-Light ™ ELL manuafactured by Quantex of Rockville, Md.

FIG. 1 shows an experimental set-up used to study the spatial behavior of the ELL light modulation using a square wave driving signal. When the ELL was moved across the observation point, scanning plots of light modulation versus position on the light-emitting area were obtained, as shown in FIG. 2. From FIG. 2 it can be seen that the whole light-emitting area is modulated nearly homogeneously.

Figure 3:
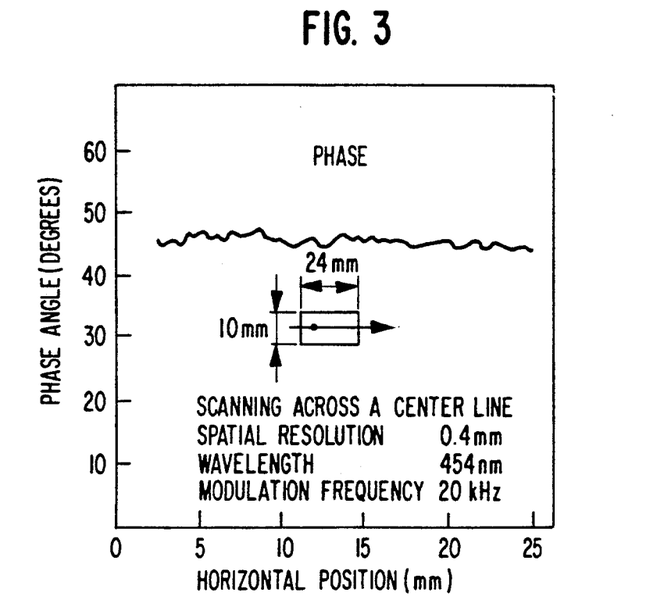
FIG. 3 is a graph of light modulation phase angle versus horizontal position across the same area of the ELL.

A similar scanning plot of the light modulation phase angle versus position was obtained by using the experimental set-up, as shown in FIG. 3. The phase angle is shown as being nearly constant across the whole lamp area.

Thus, it can be seen that the entire light-emitting area of the ELL can be utilized as an intensity-modulated light source. As the light-emitting area of the ELL can be made very large, when the ELL is arranged close to a large-size luminescent chemical sensor, a correspondingly large number of luminescence photons are obtained, thereby permitting the luminescence radiation to be detected by a relatively less sensitive (and less expensive) photodiode, rather than by a sensitive (and more expensive) photomultiplier tube.

A large output area of the ELL can also be used to detect emitted luminescence of an excited luminescent molecule over a large area, such that simultaneous or sequential multiple measurements of changes in decay time, phase angle and/or modulation of the emitted luminescence of at least one luminescent molecule, wherein are detected as parameters that correspond to multiple changes luminescence lifetimes, such as changes due to the presence of an one or more analytes in different concentrations or samples.

Photodetectors can be used to detect multiple changes in multiple samples as changes in decay time, phase angle and/or modulation of the emitted luminescence using sequential pixel measurements recorded using a processor. Such a microprocessor can process, store and analyze such data, e.g., according to U.S. Pat. No. 4,778,593 Yamashita et al, which is entirely incorporated by reference. Alternatively, such multiple changes in decay time, phase angle and/or modulation of the emitted luminescence can be detected simultaneously using a photocathode, wherein multidimensional changes are recorded using a microprocessor, e.g., according to U.S. patent application Ser. No. 07/645,525, which is entirely incorporated by reference.

Figure 4:
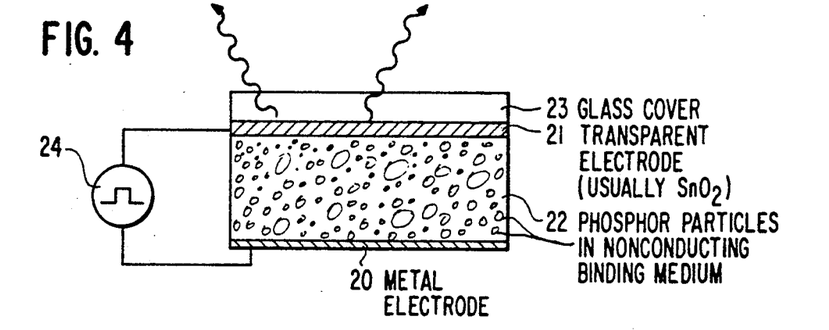
FIG. 4 is a cross-sectional view of an ELL used in accordance with the invention.

In FIG. 4 there is shown an alternating current ELL 19 containing phosphor particles suspended within a transparent insulating medium 22 sandwiched between a first electrode 20 and a second electrode 21. The second electrode 21 is made of a transparent material to allow photons to be projected outward. When a square wave (alternating voltage) is applied to the electrodes from signal generator 24, typically at a frequency in range of 500 Hz to 50 kHz, the phosphor particles emit light pulses. When a sine-wave (alternating voltage) is applied to the electrodes from signal generator 24, typically at a frequency in range of about 10 kHz to 100 kHz, the phosphor particles emit modulated light.

In FIG. 4, a voltage signal generator 24 applies an alternating square-wave input driving signal across the electrodes 20 and 21 of the ELL 19. Phosphor particles are suspended in a transparent insulating medium 22 sandwiched between the two electrodes 20 and 21. As a result of the alternating electric field, the ELL produces a series of output light pulses at twice the square-wave driving frequency, wherein the pulses contain higher frequency harmonics.

Figure 5:
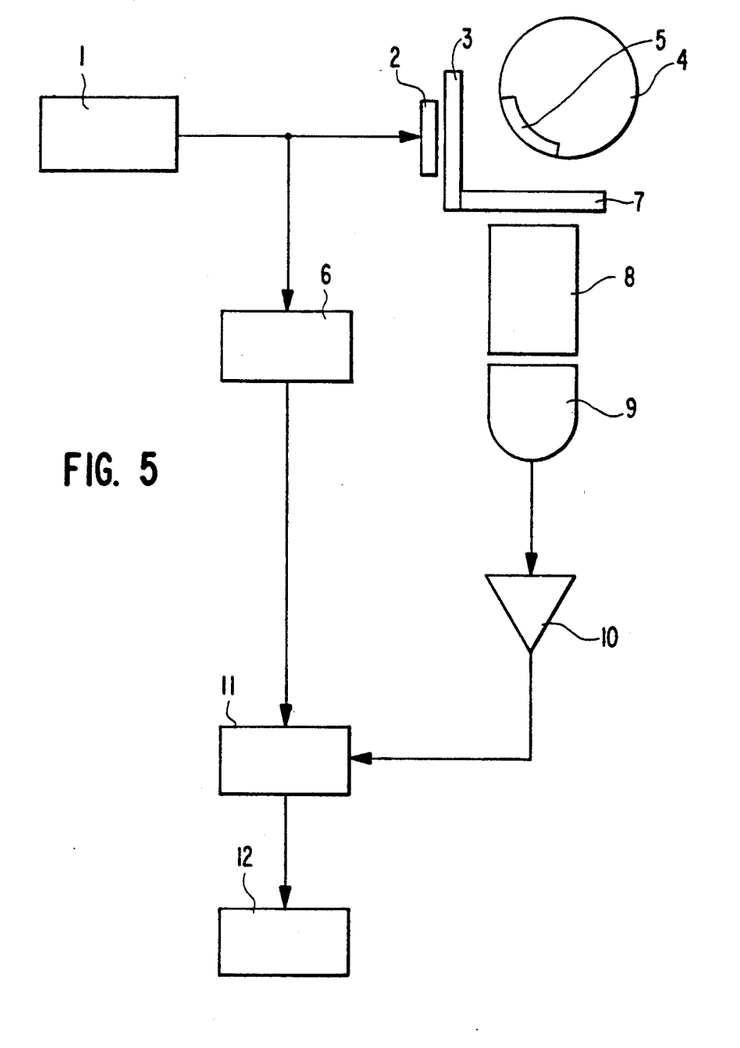
FIG. 5 is a schematic block diagram of an apparatus using a square-wave driven ELL as an excitation source for a fluorophore.

A square-wave or sine-wave driven ELL fluorometer is presented in FIG. 5 as a schematic block diagram of a phase fluorometry apparatus using a large-size, planar surface modulated ELL 2 as the excitation source in a spectroscopic oxygen sensor according to the present invention.

In operation, a square-wave signal generator 1 applies an AC signal voltage to the ELL 2 at a frequency of about 100 Hz to 100 kHz and preferably from about 500 Hz to about 50 kHz. Alternatively, a sine-wave signal generator 1 applies an AC signal voltage to the ELL 2 at a frequency of about 1 kHz to 1 MHz and preferably from about 10 kHz to 100 kHz.

The ELL 2 can be a UV, visible or near infrared wavelength emitting ELL, driven by a signal generator, such as a voltage signal generator, wherein a first electrical signal produced by the signal generator provides an alternating square-wave or sine-wave signal having a fundamental frequency that results in an emitted wavelength of the ELL that corresponds to the excitation wavelength of the luminescent molecule to be irradiated. However, to a first approximation, the modulation frequency is not substantially related to the color of the light output.

In response to the first electrical signal, as a square-wave signal or a sine-wave signal applied to the ELL, the ELL outputs a series of output light pulses or modulated output light which excite at least one luminescent molecule at its excitation wavelength to produce at least one luminescence emission having a particular lifetime.

Optionally, the ELL output can be passed through an excitation filter 3 (which substantially eliminates extraneous output light at longer wavelengths). As a result, the luminescent molecule 5 emits a luminescence photon (dependent upon the luminescent molecule used) which is detected by a photodetector, wherein the photodetector detects less extraneous output light.

Optionally, the emission passes through an emission filter 7 (which transmits luminescent radiation and eliminates or substantially reduces scattered excitation light as well as ambient light) and a fiber optic light guide 8. The light guide 8 (such as a fiber optic light guide) can act as a shield against the substantial electromagnetic interference which might otherwise be introduced by the high driving voltage applied to the ELL.

A photodetector 9 (e.g., in the form of a PIN photodiode) detects the luminescence emitted by the excited luminescent molecule. The photodetector 9 outputs a second electric signal representative of the luminescence radiation. For example, the second electrical signal can be applied through a current-to-voltage converter 10 to an input of a vector voltmeter 11. Another input of the vector voltmeter 11 receives the first electrical signal as the driving signal for the ELL.

Optionally, the first electrical signal can be inputted into a frequency multiplier 6 to provide a third electric signal having a frequency equal to one harmonic of the first electrical signal, wherein the third electrical signal is synchronized with the first electrical signal as a reference signal representative of the ELL output light pulses used to excite the at least one luminescent molecule.

The voltmeter 11 reading is thus a measure of the shift or change in decay time, phase and/or modulation of the luminescence emission relative to the phase of the (reference) exciting light from the ELL. An amplitude-time (Y-T) recorder 12 may optionally be used to record the readings of the voltmeter 11.

In the context of the present invention, the term "meter" refers to a measuring device which can determine differences in phase or modulation between two or more electrical signals, as would be apparent to one skilled in the art. For example, a voltmeter can be used as a meter, as described above.

Therefore, it can be seen that the lifetime of the luminescence can be measured through a comparison of the decay times, relative phases and or modulations of the first and second electric signals, respectively. As shown by equation (1) above, the measured phase shift angle is a function of the luminescence lifetime and of the modulation frequency of the input signal.

Thus, in accordance with one preferred embodiment of the present invention, an inexpensive intensity-modulated ELL excitation light source is driven by a square-wave or sine-wave input voltage signal. The resulting high optical output power produced by the ELL allows the use, in a phase spectroscopic sensor, of a less sensitive and inexpensive luminescence radiation detector, such as a PIN photodiode, instead of a photomultiplier tube or other extremely sensitive (and expensive) light detectors. The square-wave or sine-wave driving voltage produces a pulsed light output at a repetition rate twice the square-wave or sine-wave frequency, thereby allowing the optimization of the modulation frequency of the light source, as shown by equation (2) above. When used with suitable luminescent molecules, as further described herein, the present invention provides an increased accuracy of the lifetime measurement.

Photosensitive devices as photodetectors suitable for use in methods and apparatus of the present invention include, e.g., photomultiplier tubes (PMTs); microchannel plate PMTS; photodiodes including silicon, germanium, and gallium arsenide; avalanche photodiodes; photoresistors; photoconductive cells; photo-regenerative devices; photoelectric cells; and charge-coupled devices. Such photosensitive devices, used as photodetectors in the present invention, can be used singly or in arrays, as would be known in the art for photodetection of an ELL light source.

Alternative apparatus suitable for use in the present invention can be used with an ELL (from, e.g., as manufactured by Quantex of Rockville, Maryland) include a square wave signal generator or a sine-wave signal generator, as described herein.

Additionally, the wide variety of sizes available for ELLS allows the present invention to be used in many other applications. For example, a large area ELL can be utilized as an excitation light source for chemical sensors. Also, a large area ELL can be used as an excitation source for a matrix of sensors by partitioning the transparent electrode (see, e.g., FIG. 4) into pixels defining a particular spatial resolution.

Thus, in accordance with the present invention, there is provided an ELL having a modulated electrical input and producing a large number of photons which excite a luminescent material to emit luminescence radiation which can be detected by inexpensive light detectors, such as large area PIN photodiodes. The modulated input can be a square-wave driving signal which produces a pulsed light output or a sine-wave driving signal. The ELL can be combined with a luminescent chemical sensor in a phase spectroscopic system to detect concentration levels of chemicals (e.g., oxygen) in a sample.

Example 1

Apparatus for Luminescence Measurement Using an ELL as a Light Source

A specific example of an ELL spectrometer as presented in FIG. 5 is a schematic block diagram of a phase spectrometry apparatus using a large-size, planar surface modulated ELL 2 as the excitation source in a fluorometric oxygen sensor according to the present invention. In operation, the square-wave signal generator I applies a first AC signal voltage to the ELL 2 at a frequency of 10 kHz.

The ELL 2 is a 10 mm×24 mm, 454 nm violet-emitting PermaLight~ELL, e.g., as manufactured by Quantex of Rockville, Maryland. The measured optical output power of this ELL (when driven by a 10 kHz square-wave) is 118 times the optical power measured from a Siemens model LDB5410 blue-emitting silicon carbide LED operated at 25 mA forward current. The voltage signal generator is a BK Precision model 3020 sweep/function generator plus a transformer.

In response to the square-wave voltage signal applied to the ELL, the ELL outputs a series of output light pulses which are passed through an attached Corning 5-56 excitation filter 3 (which eliminates extraneous output light at longer wavelengths) to an active fluorophore-containing membrane sensor 5 within a vial 4. As a result, the fluorophore in the sensor 5 emits fluorescence radiation (dependent upon the fluorophore used) which passes through a Corning 6-21 emission filter 7 (which transmits radiation above 610 nm and eliminates or substantially reduces scattered excitation light as well as ambient light) and a fiber optic light guide 8. The light guide 8 acts as a shield against possible electromagnetic interference which might otherwise be introduced by the high driving voltage applied to the ELL.

A fluorescence detector in the form of a PIN photodiode 9 (as a Hamamatsu model S2744-03 large-area PIN silicon photodiode with a 10 mm×20 mm sensitive area) measures the fluorescence emitted by the fluorophore in the sensor. The photodiode 9 outputs a second electric signal representative of the fluorescence radiation through a current-to-voltage converter 10 (an Analog Devices model 43J operational amplifier) to an input of a vector voltmeter 11 (a PAR model 5204). Another input of the vector voltmeter 11 receives from a frequency multiplier 6 a third electric signal synchronized with the first signal and representative of the ELL output light pulses used to excite the fluorophore. The voltmeter reading is a measure of the shift or change in phase and/or modulation of the emitted fluorescence relative to the phase and/or modulation of the (reference) exciting light from the ELL. An amplitude-time (Y-T) recorder 12 is used to record the readings of the voltmeter 11.

Therefore, it can be seen that the lifetime of the fluorescence can be measured through a comparison of the relative phases of the electric signals output by the frequency multiplier 6 and the PIN photodiode 9, respectively. As shown by equation (1) above, the measured phase shift angle is a function of the fluorescence lifetime and of the modulation frequency selected by means of a frequency multiplier 6.

Figure 6:
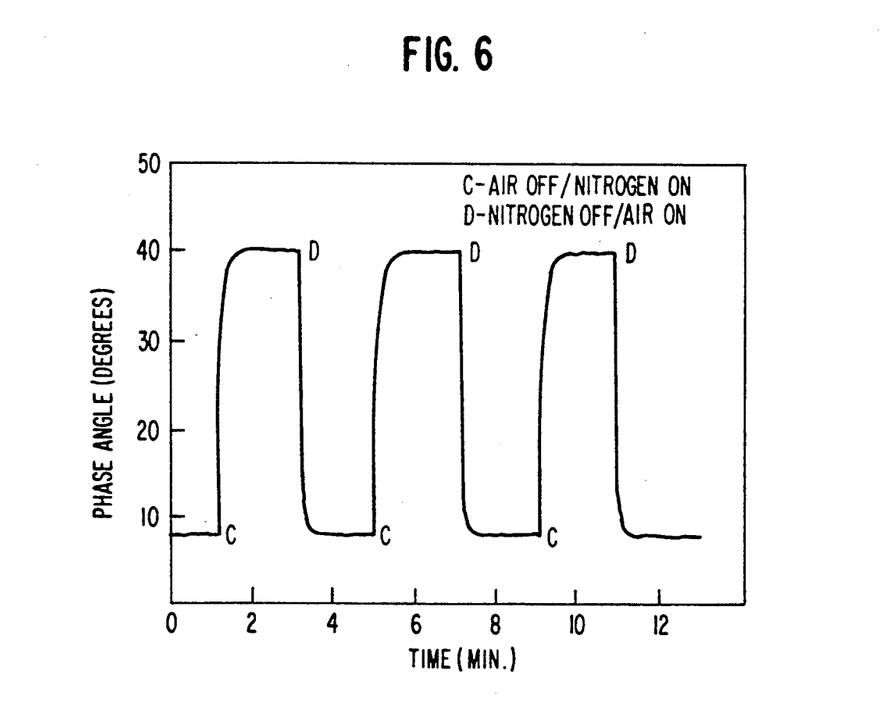
FIG. 6 is a graph of changes, in response to oxygen changes caused by alternating nitrogen- and air-flushing, of fluorescence phase angles for a ruthenium-based fluorophore embedded in a silicone matrix.

Results provided by the above apparatus are presented in FIG. 6, wherein changes in response to oxygen changes are presented which are caused by alternating nitrogen- and air-flushing of fluorescence phase angles for a ruthenium-based fluorophore embedded in a silicone matrix.

The present invention is thus shown to reproducibly use an ELL to provide accurate and sensitive measurements in changes in decay time, phase angle and/or modulation, corresponding to changes in luminescence lifetimes that can be used to detect or quantify an analyte in a sample.

A particular alternative embodiment of the present invention includes monitoring luminescence lifetime changes using time-domain techniques. However, phase-modulation is less expensive since time-domain apparatus would be more expensive than phase modulation apparatus.

Other objects, features and advantages of the present invention will become apparent to those skilled in the art from the above detailed description and examples of the present invention. It should be understood, however, that the description and specific examples, while indicating preferred embodiments of the present invention, are given by way of illustration and not limitation. Many changes and modifications within the scope of the present invention may be made without departing from the spirit thereof, and the present invention includes all such modifications.

What is claimed is:

1. An apparatus for detecting a change in decay time, phase angle and/or modulation, corresponding to a change in a lifetime, of a luminescence emission of at least one luminescent molecule comprising:

an electroluminescent lamp which outputs modulated light when driven by a first electrical signal;

a first electrical signal generator, coupled to said electroluminescent lamp, for generating said first electrical signal to cause said electroluminescent lamp to output said modulated light having a wavelength which excites said at least one luminescent molecule to produce said luminescence emission;

a photosensor for detecting said luminescence emission and generating a second electrical signal corresponding to said luminescence emission;

a meter coupled to said photosensor and said first electrical signal, wherein said meter compares said first electrical signal to said second electrical signal to provide said change in decay time, phase angle and/or modulation of said luminescence emission of said at least one luminescent molecule, wherein said change corresponds to said change in a luminescence lifetime of said luminescent molecule.

2. The apparatus of claim 1, wherein said electroluminescent lamp outputs said modulated light with a plurality of frequency components that are harmonics of said first electrical signal.

3. The apparatus of claim 1, wherein said wavelength of said modulated light is in the range of 250-1000 nm.

4. The apparatus of claim 1, wherein said modulated light is intrinsically or extrinsically modulated at a frequency range of 200 Hz to 10 MHz.

5. The apparatus of claim 4, wherein said modulated light is intrinsically or extrinsically modulated at a frequency range of 1 kHz to 10 MHz.

6. The apparatus according to claim 1, wherein said detecting is done in one selected from frequency-domain, time-domain or phase/modulation.

7. The apparatus of claim 1, wherein said photosensor is optically coupled to said luminescence emission via at least one selected from a lens system and proximity focused geometry.

8. The apparatus of claim 1, wherein said luminescent molecule has a lifetime of at least 25 nanoseconds.

9. The apparatus of claim 1, wherein said first electrical signal is a square wave signal.

10. The apparatus of claim 9, wherein said first electrical signal is modulated at a fundamental frequency of at least 500 Hz.

11. The apparatus of claim 10, wherein a third electrical signal is generated by a second electrical signal generator synchronized to said first electrical signal, and wherein said meter compares said second electrical signal and said third electrical signal to provide said change in decay time, phase angle and/or modulation of said luminescence emission of said at least one luminescent molecule, wherein said change corresponds to said change in a luminescence lifetime of said luminescent molecule.

12. The apparatus of claim 11, wherein said second electrical signal generator is a frequency multiplier.

13. The apparatus of claim 1, wherein said first electrical signal is a sine wave signal.

14. The apparatus of claim 13, wherein said first electrical signal is modulated at a fundamental frequency of at least 10 kHz.

15. The apparatus of claim 13, wherein said third electrical signal is synchronized with said first electrical signal.

16. The apparatus of claim 9 wherein said photosensor comprises a first photodiode.

17. The apparatus of claim 1 wherein said photosensor comprises at least one selected from a photomultiplier tube, a photodiode, or a charged coupled device.

18. The apparatus of claim 16 wherein said first photodiode comprises a PIN photodiode.

19. A method of using an electroluminescent lamp as a high-frequency modulated light source, comprising detecting a change in decay time, phase angle and/or modulation, corresponding to a change in a lifetime of a luminescence emission of at least one luminescent molecule.

20. A method according to claim 19, wherein said change in decay time, phase angle and/or modulation corresponds to the presence of an analyte, such that said method provides for sensing said analyte.

21. A method for detecting a change in decay time, phase angle and/or modulation, corresponding to a change in a lifetime, of a luminescence emission of at least one luminescent molecule comprising:

driving an electroluminescent lamp with a first electrical signal to cause said electroluminescent lamp to output modulated light having a wavelength which excites said at least one luminescent molecule in a sample to produce said luminescence emission;

exciting said at least one luminescent molecule with said modulated light to produce a luminescence emission;

detecting said luminescence emission with a photosensor to produce a second electrical signal corresponding to said luminescence emission;

comparing said first electrical signal to said second electrical signal to provide said change in decay time, phase angle and/or modulation of said luminescence emission of said at least one luminescent molecule, wherein said change corresponds to said change in a luminescence lifetime of said luminescent molecule.

22. The method of claim 21, wherein said electroluminescent lamp outputs said modulated light with a plurality of frequency components that are harmonics of said first electrical signal.

23. The method of claim 21, wherein said wavelength of said modulated light is in the range of 250-1000 nm.

24. The method of claim 21, wherein said output of said modulated light is intrinsically or extrinsically modulated at a frequency range of 200 Hz to 10 MHz.

25. The method of claim 24, wherein said output of said modulated light is intrinsically or extrinsically modulated at a frequency range of 1 kHz to 10 MHz.

26. The method according to claim 21, wherein said method is one selected from frequency-domain, time domain or phase/modulation.

27. The method of claim 21, wherein said photosensor is optically coupled to said luminescence emission via at least one selected from a lens system or proximity focused geometry.

28. The method of claim 21, wherein said luminescent molecule has a lifetime of at least 25 nanoseconds.

29. The method of claim 21, wherein said first electrical signal is a square wave signal.

30. The method of claim 29, wherein said first electrical signal is modulated at a fundamental frequency of at least 100 Hz.

31. The method of claim 30, wherein a third electrical signal, synchronized to said first electrical signal, is generated by a second electrical signal generator.

32. The method of claim 29, wherein said second electrical signal generator is a frequency multiplier.

33. The method of claim 21, wherein said first electrical signal is a sine wave signal.

34. The method of claim 33, wherein said first electrical signal is modulated at a fundamental frequency of at least 10 kHz.

35. The method of claim 33, wherein a third electrical signal is generated by a second electrical signal generator and is synchronized with said first electrical signal.

36. The method of claim 29 wherein said photosensor comprises a first photodiode.

37. The method of claim 21 wherein said photosensor comprises at least one selected from a photomultiplier tube, a photodiode, or a charged coupled device.

38. The method of claim 36 wherein said first photodiode comprises a PIN photodiode.

39. The method of claim 21, wherein said change corresponds to the presence or concentration of an analyte in a sample, wherein said sample is a compound, a mixture, a surface, a solution, an emulsion, a suspension, a mixture, a cell culture, a fermentation culture, a cell, a tissue, a secretion or a derivative or extract thereof.

40. A method according to claim 21, wherein said analyte comprises a salt, a derivative, a polymer, a dissociation product, or aggregate of said analyte.

41. A method according claim 39, wherein said analyte is selected from $H^+$, $OH^-$, $CO_2$, $H_2HCO_3^{3-}$, $Ca^{++}$, $Na^+$, $Mg^{++}$, or $K^+$.

42. A method according to claim 39, wherein said method comprises a frequency-domain luminescence lifetime measurement, a time-domain luminescence lifetime measurement, a phase angle luminescence lifetime measurement, a phase-sensitive luminescence lifetime measurement, or a modulation luminescence lifetime measurement.

43. An apparatus for measuring luminescence comprising:
    an electroluminescent lamp (ELL) which produces light when driven by an electrical input signal;
    an electrical input signal generator, coupled to said ELL, for generating an electrical input signal which drives said ELL;
    at least one luminescent molecule for determining a condition and emitting a characteristic luminescence upon incidence of light output from said ELL; and
    light-detecting means for detecting the lifetime of said luminescence as a measurement of said condition.

44. A method of continuously generating light pulses from an electroluminescent lamp (ELL) having a luminescence material disposed between electrodes, said method comprising:
    continuously applying a square wave input voltage signal to said electrodes of said ELL; and
    rapidly and continuously alternating the polarity of the voltage of said square wave input signal so that said luminescence material continuously generates a corresponding pulsed light output waveform.

45. An apparatus for measuring luminescence comprising:
    an electroluminescent lamp (ELL) which outputs pulses of light when driven by an amplitude-modulated electrical input signal;
    an electrical input signal generator, electrically coupled to said ELL, for generating a square-wave electrical input signal whose transition time from a positive voltage to a negative voltage is less than or equal to 1 $\mu s$, so that the light pulses have a repetition frequency which is a harmonic of twice the modulation frequency of said electrical input signal;
    a chemical sensor for determining a condition and emitting luminescence upon incidence of the light output from said ELL; and
    light-detecting means for detecting said luminescence as a measurement of said condition.

46. A method of measuring luminescence, comprising the steps of:
    driving an electroluminescent lamp (ELL) with an alternating input voltage signal whose transitions from a positive voltage to a negative voltage cause the ELL to output pulses of light;
    exciting a luminescent molecule with the pulses of light from the ELL; and
    detecting resulting emitted luminescence radiation from the luminescent molecule.

47. The method of claim 46, further comprising the step of driving the ELL with a sine-wave input voltage signal.

48. The method of claim 46, further comprising the step of driving the ELL with a square wave input voltage.

49. The method of claim 46, further comprising the step of measuring the lifetime of the detected luminescence by measuring a phase difference between said emitted luminescence and the pulses of light from the ELL.

50. The apparatus of claim 1, wherein said first electrical signal generator generates said first electrical signal as a square-wave having a frequency at least as high as 500 Hz to produce the modulated light as periodic light pulses which have a pulse repetition frequency equal to twice the frequency of the square-wave signal, and each of which has a full width at half maximum (FWHM) of at least as short as 1 $\mu sec$.

51. The method claim 21, wherein said first electrical signal is a squarewave signal having a frequency at least as high as 500 Hz to produce the modulated light as periodic light pulses which have a pulse repetition frequency equal to twice the frequency of the square-wave signal, and each of which has a full width at half maximum (FWHM) of at least as short as 1 $\mu sec$.

52. The apparatus of claim 43, wherein said electric input signal generator generates said electrical input signal as a square-wave signal having a frequency at least as high as 500 Hz to produce the modulated light as periodic light pulses which have a pulse repetition frequency equal to twice the frequency of the square-wave signal, and each of which has a full width at half maximum (FWHM) of at least as short as 1 $\mu sec$.

53. The method of claim 44, wherein said input voltage signal is a square-wave signal having a frequency at least as high as 500 Hz to produce the modulated light as periodic light pulses which have a pulse repetition frequency equal to twice the frequency of the square-wave signal, and each of which has a full width at half maximum (FWHM) of at least as short as 1 $\mu sec$.

54. The method of claim 48, wherein said square-wave input voltage has a frequency at least as high as 500 Hz to generate the modulated light in the form of periodic light pulses which have a pulse repetition frequency equal to twice the frequency of the square-wave signal, and each of which has a full width at half maximum (FWHM) of at least as short as 1 $\mu sec$.

55. An apparatus for generating light pulses, comprising:
    an electroluminescent lamp having a luminescence material disposed between two electrodes; and
    means for applying across said electrodes a square wave voltage signal that continuously alternates in polarity at a frequency of at least 500 Hz to cause said lamp to generate a correspondingly continuous train of periodic light pulses each of which has a full width at half maximum (FWHM) of at least as short as 1 $\mu sec$.

* * * * *